US00PP17148P2

(12) United States Plant Patent
Danziger

(10) Patent No.: US PP17,148 P2
(45) Date of Patent: Oct. 10, 2006

(54) ***SOLIDAGO* PLANT NAMED 'DANSOL21'**

(50) Latin Name: ***Solidago* sp.**
Varietal Denomination: Dansol21

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/202,038

(22) Filed: Aug. 12, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
*Assistant Examiner*—June Hwu
(74) *Attorney, Agent, or Firm*—Foley & Lardner LLP

(57) ABSTRACT

A new and distinct *Solidago* plant named 'Dansol21' particularly characterized by having a plant height of 70–75 cm, large, yellow inflorescences, green leaves, a rapid growth cycle and an even growth rate.

2 Drawing Sheets

Botanical designation: *Solidago* sp.
Variety denomination: 'Dansol21'.

BACKGROUND OF THE INVENTION

The present invention relates to a new and distinct cultivar of the goldenrod plant, botanically known as *Solidago* sp., and hereinafter referred to by the cultivar name 'Dansol21'.

*Solidago,* of the sunflower family, Asteraceae, consists of approximately 100 species of goldenrod plants found in North America, most of which are geographically located in the East. Goldenrods are perennial plants that commonly grow along stream banks, ditches, roadsides and other areas where the soil is moist and rich.

The new *Solidago* cultivar is a product of a planned breeding program conducted by the inventor, Gabriel Danziger, in Moshav Mishmar Hashiva, Israel. The objective of the breeding program was to develop a new *Soligado* variety with a large yellow inflorescence, green leaves, a rapid growth cycle, and an even growth rate.

The new *Solidago* cultivar originated from a cross made by a planned breeding program discovered by the inventor in 2001 in Moshav Mishmar Hashiva, Israel. The female or seed parent is *Solidago* sp. cultivar designated as '4-gy-8' (unpatented). The male or pollen parent is unknown. The new *Solidago* cultivar 'Dansol21' was selected by the inventor as a flowering plant within the progeny of the stated cross in a controlled environment in Moshav Mishmar Hashiva, Israel.

Asexual reproduction of the new *Solidago* cultivar by leaf cuttings was first performed in October, 2001, in Moshav Mishmar Hashiva, Israel, and has demonstrated that the combination of characteristics as herein disclosed for the new *Solidago* cultivar are firmly fixed and retained through successive generations of asexual reproduction. The newly cultivar reproduces true to type.

BRIEF DESCRIPTION OF THE INVENTION

The following traits have been repeatedly observed and are determined to be unique characteristics of 'Dansol21' which in combination distinguish this *Solidago* as a new and distinct cultivar:

1. Large, yellow inflorescences;
2. 70 to 75 cm in height;
3. Green leaves;
4. Rapid growth cycle; and
5. Even growth rate.

Plants of 'Dansol21' differ from plants of the female parent, '4-gy-8' (unpatented) primarily in branch and inflorescence strength. 'Dansol21' has sturdier branches and denser inflorescences than the mother plant.

Of the many commercial cultivars known to the present inventor, the most similar in comparison to 'Dansol21' is the *Solidago* cultivar 'Tara' (unpatented). 'Dansol21' has larger, yellow inflorescences than 'Tara'. The inflorescences of 'Tara' are a lighter yellow color, most similar to yellow group, RHS 7A, whereas the inflorescences of 'Dansol21' are most similar to yellow group, RHS 12A.

BRIEF DESCRIPTION OF THE DRAWINGS

The accompanying photographic drawings illustrate the overall appearance of the new *Solidago* cultivar 'Dansol21' showing the colors as true as is reasonably possible with colored reproductions of this type. Color in the photographs may differ slightly from the color value cited in the detailed botanical description, which accurately describe the color of 'Dansol21'.

DETAILED BOTANICAL DESCRIPTION

Figure 1:
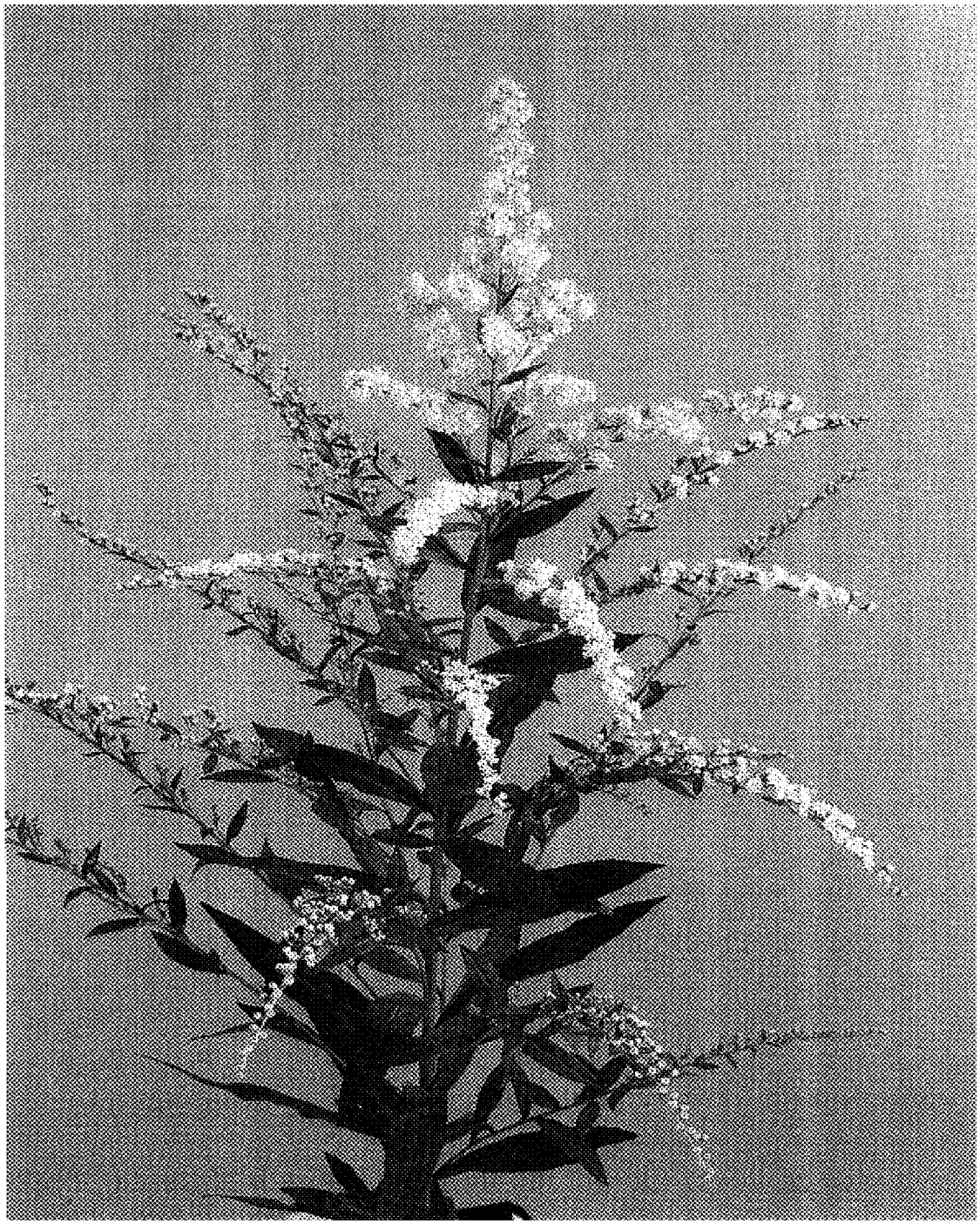
FIG. 1 shows a side view perspective of a typical, potted 'Dansol21' at the age of 10 weeks.
Figure 2:
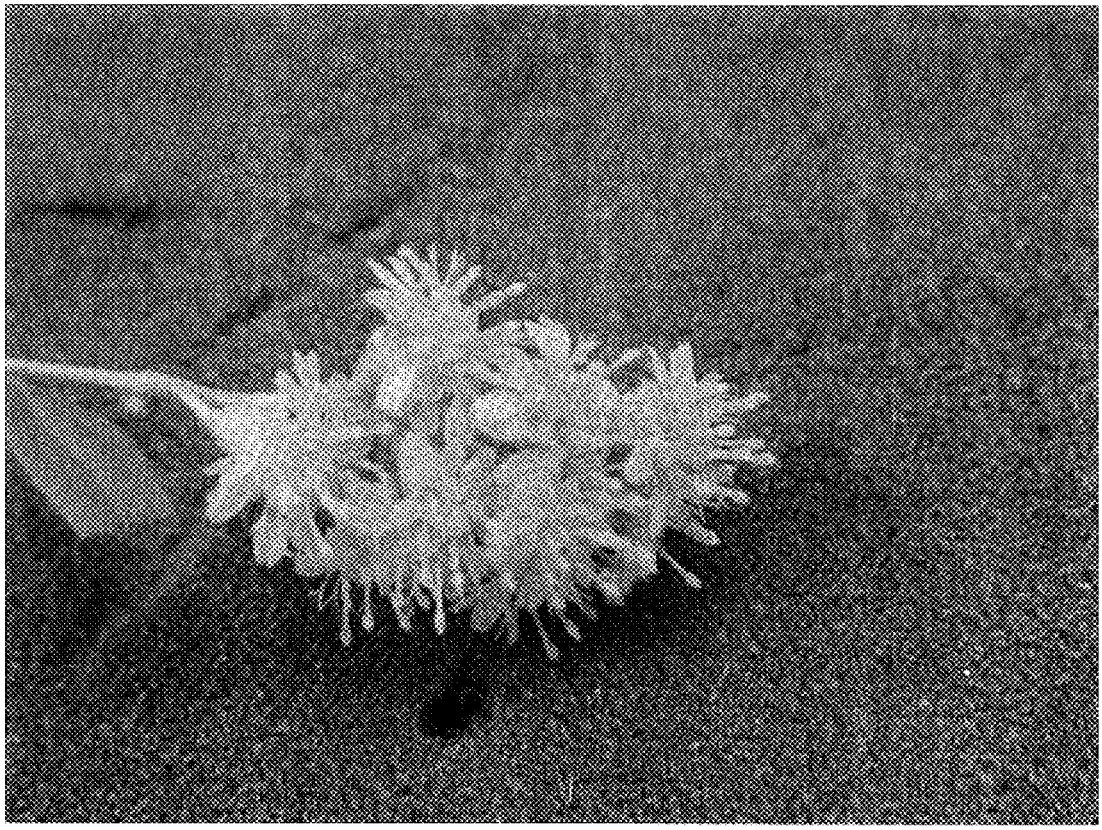
FIG. 2 shows a close-up of yellow inflorescence of 'Dansol21' at the age of 10 weeks.

The new *Solidago* cultivar 'Dansol21' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new *Solidago* cultivar as grown in the field in Moshav Mishmar Hashiva, Israel, under conditions which closely approximate those generally used in commercial practice. The photographs and descriptions were taken during May 2004, when the outdoor day temperature averaged 27° C. and the outdoor night temperature averaged 20° C. The plant was grown with fertilization N:P205:K20 in the ratio of 5:3:8. The age of plants described is 10 weeks.

Color references are made to The Royal Horticultural Society Colour Chart (R.H.S.), 2001 edition, except where general colors of ordinary significance are used. Color values were taken under daylight conditions at approximately 12:00 p.m. in Moshav Mishmar Hashiva, Israel.

Classification:

*Botanical.*—*Solidago* sp.

Parentage:

*Female or seed parent.*—*Solidago* sp. seedling designated '4-gy-8' (unpatented).

*Male or pollen parent.*—Unknown.

Propagation:

*Type.*—Tip cutting.

*Time and temperature to initiate and develop roots.*—Summer: Time: 10 days to initiate roots, 21 days for a rooted plant. Temperature: Night 25° C., Day 35° C. Winter: Time: 14 days to initiate roots, 25 days for a rooted plant. Temperature: Night 18° C., Day 25° C. Root description: Fibrous Roots.

Plant:

*Crop time.*—From cuttings, about 10 weeks are required to produce a finished flowering plant.

*Plant form.*—Perennial, goldenrod decorative plant; dense and bushy.

*Growth habit.*—Vigorous.

*Height.*—70 to 75 cm.

*Width* (*diameter*).—25 cm.

*Branching habit and arrangement.*—About 4 to 5 stems, when pinched, rising together from main stem base.

*Cold tolerance.*—Hardy in moderate climate, approximately to 5° C.

*Stems.*—Number of stems: About 4 to 5 stems, when pinched. Length: 75 cm. Width (diameter): 2.3 to 2.5 cm. Internode length: 4.0 to 4.5 cm. Strength: Sturdy. Texture: Pubescent.

*Foliage.*—Quantity: About 20 leaves per stem. Length: 11.0 cm. Width: 1.5 cm. Overall shape: Lanceolate. Shape at apex: Acute. Shape at base: Acute. Texture: Puberulous. Margin: Toothed. Color of mature leaf: Upper surface: Green, RHS 137B. Lower surface: Green, RHS 137C. Color of immature leaf: Upper surface: Green, RHS 138A. Lower surface: Green, RHS 138B. Venation: Pattern: Observed, extending from leaf surface. Midrib with secondary veins. Color: Green, RHS 138B.

*Petioles.*—Length: 3 mm. Diameter: 4 mm. Color: Green, RHS 143D.

Inflorescence:

*Type and habit.*—Free-flowing, upward-facing and elongated panicles. Ray and disc florets arranged acropetally on a capitulum.

*Quantity of inflorescences per plant:*—Couple of hundred.

*Fragrance.*—Medium fragrance.

*Flowering response.*—Under natural conditions, plants flower in late summer. At other times of year, flower initiation and development can be induced under (long day) conditions. Response time is 10 weeks.

*Post-production longevity.*—Cut inflorescences maintain for about 14 days with no fading. On the plant, inflorescences maintain for about 1–2 weeks.

*Inflorescence diameter.*—6 mm.

*Inflorescence depth* (*height*).—6 mm.

*Panicle length.*—34 cm.

*Panicle diameter.*—19 cm.

*Disc diameter.*—3 cm.

*Buds.*—Length: 5 mm. Diameter: 2 mm. Shape: Ellipsoid. Rate of opening: About 4 to 5 days. Color: Green, RHS: 144C, below, and yellow, RHS: 13A, above.

*Ray florets:*—Number of rays per inflorescence: 1 row of petals. Number of inflorescence per row: About 10 to 13 in one row. Length: 2.0 mm. Width: 1 mm. Overall shape: Oblong. Shape at apex: Rounded. Shape at base: Wedge shaped. Margin: Entire. Texture: Smooth. Aspect: 60° from vertical. Color (upper surface): Yellow group, RHS 12A. Color (under surface): Yellow group, RHS 12A.

*Disc florets.*—Number of discs per inflorescence: About 4 to 6. Length: 2 mm. Diameter: 1 mm. Overall shape: Spoon shaped. Shape at apex: Blunt. Shape at base: Pointed. Color (mature): Yellow, RHS 13A. Color (immature): Yellow, RHS 13A.

*Involucral bracts.*—Number per inflorescence: About 6 to 10. Length: 0.3 cm. Width: 0.1 cm. Shape: Oblong. Shape at apex: Rounded. Shape at base: Attenuate. Margin: Entire. Texture: Pubescent. Color (upper surface): Yellow-green, RHS 144A to 144B. Color (under surface): Yellow-green, RHS 144B to 144C.

*Peduncles.*—Length: 0.5 cm. Strength: Sturdy. Angle: About 45° to the stem. Texture: Puberulent. Color: Yellow-green, RHS N144 D.

Reproductive organs:

*Androecium.*—Location: On disc florets only. Anthers: Number: 4 to 6. Size: 1 mm. Pollen: Amount: Abundant. Color: Yellow, RHS 13A.

*Gynoecium.*—Location: On ray and disc florets only. Pistils: Number: 6 to 10. Size: 1 mm. Color: Yellow, RHS 13B.

Seeds:

*Quantity.*—6 to 10.

*Size.*—1 mm.

*Color.*—Greyish-brown, RHS 199C.

Fruit: None observed.

Disease/pest resistance/susceptibility: Not tested; no information is currently available.

I claim:

1. A new and distinct *Solidago* plant named 'Dansol21', substantially as illustrated and described herein.

* * * * *